(12) United States Patent
Boese et al.

(10) Patent No.: US 8,027,526 B2
(45) Date of Patent: Sep. 27, 2011

(54) METHOD FOR PROVIDING A 3D X-RAY IMAGE DATASET OF A PATIENT'S HEART

(75) Inventors: Jan Boese, Eckental (DE); Joachim Hornegger, Effeltrich (DE); Günter Lauritsch, Erlangen (DE); Marcus Prümmer, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 1001 days.

(21) Appl. No.: 11/980,229

(22) Filed: Oct. 30, 2007

(65) Prior Publication Data

US 2008/0137936 A1 Jun. 12, 2008

(30) Foreign Application Priority Data

Oct. 31, 2006 (DE) .......................... 10 2006 051 919

(51) Int. Cl.
*A61B 6/03* (2006.01)
(52) U.S. Cl. ............... 382/131; 378/8; 378/95; 378/901
(58) Field of Classification Search ................ 378/8, 95, 378/901; 382/131
See application file for complete search history.

(56) References Cited

U.S. PATENT DOCUMENTS

| | | | | |
|---|---|---|---|---|
| 7,231,076 B2* | 6/2007 | Fu et al. | ......................... | 382/131 |
| 7,315,605 B2* | 1/2008 | Boese et al. | ....................... | 378/8 |
| 7,327,865 B2* | 2/2008 | Fu et al. | ......................... | 382/128 |
| 7,471,760 B2* | 12/2008 | Boese | ................. | 378/8 |
| 7,545,903 B2* | 6/2009 | Kohler et al. | ...................... | 378/8 |
| 7,593,558 B2* | 9/2009 | Boese et al. | .................. | 382/128 |
| 7,630,528 B2* | 12/2009 | Kohler et al. | ................. | 382/128 |
| 7,899,223 B2* | 3/2011 | Boese et al. | ................... | 382/128 |
| 2006/0067459 A1* | 3/2006 | Boese et al. | ...................... | 378/4 |

FOREIGN PATENT DOCUMENTS

DE   10 2004 048 209 B3   9/2005

OTHER PUBLICATIONS

M. Prummer et al., "Cardiac C-arm CT: 4D Non-Model based Heart Motion Estimation and its Application", Submission to the SPIE Medical Imaging Conference, San Diego, CA, USA, Feb. 17-22, 2007; pp. 1-12.

(Continued)

*Primary Examiner* — Allen C. Ho

(57) ABSTRACT

X-ray images are recorded of a patient's heart and the heartbeat phase is registered as that is done. The heartbeat phases are coarsely divided into intervals and all X-ray images that have been assigned heartbeat phase from the interval are used for reconstructing a 3D image dataset. The movement fields of the other 3D image datasets are then calculated for one of said 3D image datasets. Movement fields are vector fields indicating the movements of similar structures from one local area to the other. A departure is then made from the coarse interval division, and for each heartbeat phase a movement field is interpolated individually or at least for fairly short intervals from the movement fields determined in advance, which field is used for generating a deformed 3D image dataset that has been imaged onto a reference heartbeat phase. The deformed 3D image datasets are then added together.

14 Claims, 3 Drawing Sheets

OTHER PUBLICATIONS

M. Prümmer et al., "Cardiac C-arm CT: Efficient Motion Correction for 4D-FBP", Submission to the SPIE Medical Imaging Conference, San Diego, CA, USA, Oct. 29-Nov. 4, 2006; pp. 1-11.

Christopher Blondel et al., "3D Tomographic Reconstruction of Coronary Arteries using a precomputed 4D Motion Field" 2004 Phys. Med. Biol. 49, pp. 2197-2208.

Dirk Schäfer, et al., "Motion-compensated and gated cone beam filtered back-projection for 3-D rotational X-ray angiography", IEEE Trans Med Imaging. Jul. 25, 2006, pp. 898-906.

Günter Lauritsch, Jan Boese, Lars Wigström, Herbert Kemeth, Rebecca Fahrig, "Towards Cardiac C-Arm Computer Tomography"; IEEE Transactions on Medical Imaging; Jul. 2006; pp. 922-934; vol. 25, No. 7.

* cited by examiner

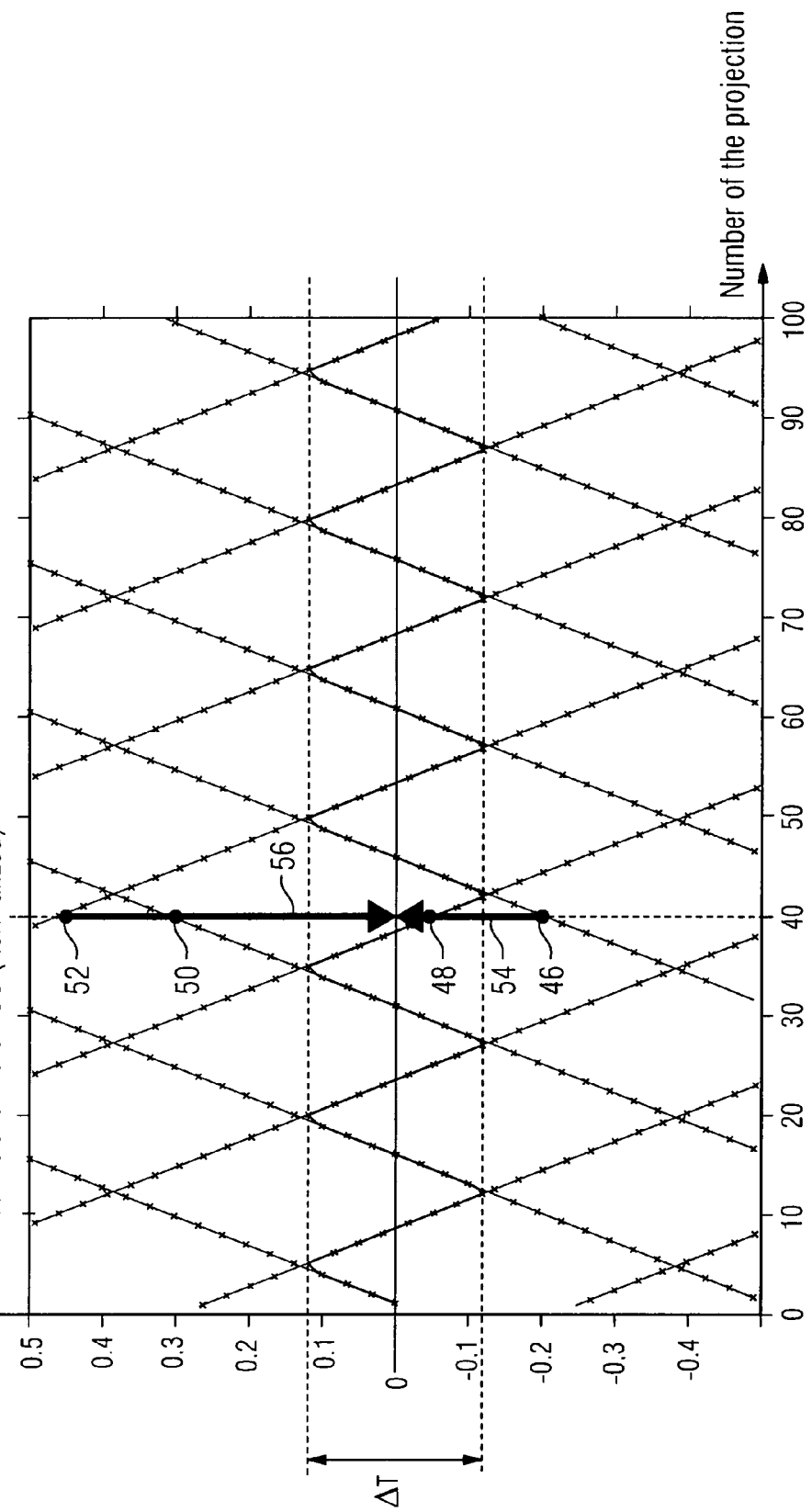

METHOD FOR PROVIDING A 3D X-RAY IMAGE DATASET OF A PATIENT'S HEART

CROSS REFERENCE TO RELATED APPLICATIONS

This application claims priority of German application No. 10 2006 051 919.1 filed Oct. 31, 2006, which is incorporated by reference herein in its entirety.

FIELD OF THE INVENTION

The invention relates to a method for providing a 3D X-ray image dataset of a patient's heart.

BACKGROUND OF THE INVENTION

A 3D image dataset is a three-dimensional field of volumetric pixels (voxels) each of which has been assigned a gray or color value.

To generate a 3D image dataset, a sequence of individual 2D images is usually recorded. The 3D image dataset is generated from the individual 2D images with the aid of what is termed a reconstruction process; with the aid of, for instance, filtered back-projection.

A particular feature associated with cardiac imaging is that the heart is in constant motion. The time usually required to record a sequence of X-ray images is longer than the heartbeat period. The 2D X-ray images can not, therefore, be readily reconstructed from a recorded sequence into a 3D X-ray image dataset to practical effect.

For that reason, the approach has instead been adopted of performing an electrocardiogram (ECG) measurement on the patient during image recording and then measuring the heartbeat phase for each recording. What is measured as the heartbeat phase is the time elapsing between the occurrence in the electrocardiogram of a reference structure (usually what is termed an R peak) and the image recording instant (or vice versa).

The knowledge about the heartbeat phase can be applied in two different ways: A first sequence of X-ray images for each of which the heartbeat phase is measured can first be recorded with the aid of an X-ray C-arm. The sequence of X-ray images corresponds to different traversing angles of the X-ray C-arm. A range of 180 degrees plus what is termed the fan angle of the X-ray source is usually traversed. The time taken overall to record the X-ray image sequences is always the same. Whereas the heartbeat phase is to be randomly selected for the first sequence of X-ray images, the knowledge about the heartbeat phase can then be used for initiating the recording of further sequences of X-ray images in a defined manner. In other words, a succeeding traversal will in each case be triggered. That can be arranged such that an interval of heartbeat phases can after a predetermined number of traversals be defined in such a way that at each angular position of the X-ray C-arm there will be precisely one (or, in a progression thereof, at least one) X-ray image that has been assigned a heartbeat phase from the interval. The greater the number of traversals, the shorter can be the interval. In the case of N traversals, the interval will usually extend across an N-th of the entire range of heartbeat phases (from reference peak to reference peak). Since for each angular position there will be a complete set of X-ray images where the heartbeat phase occurs within the interval, a 3D X-ray image dataset can be reconstructed exclusively on the basis of said X-ray images. If the interval is sufficiently small, the structures will be sufficiently well defined. If, for instance, four traversals of the X-ray C-arm are selected, then a time resolution of one fourth of the heart's beat length will be achieved, which will suffice to see the ventricles and the large branches of the coronary arteries in the reconstruction images. The greater the number of traversals, the shorter will be the interval and the more there will be to see in the reconstruction images. The method just described is explained in more detail in the article by G. Lauritsch, J. Boese, L. Wigström, H. Kemeth, and R. Fahrig, titled "Towards Cardiac C-arm Computed Tomography", appearing on pages 922 to 934 in IEEE Transactions on Medical Imaging, Vol. 25, published in 2006.

A second approach to employing the measured heartbeat phase to practical effect is described in DE 10 2004 048 209 B3.

X-ray images for each of which the heartbeat phase (cyclic relative time) has been measured are in that method grouped as a function of the measured heartbeat phase. A preliminary 3D image dataset is generated from each group. One of the 3D image datasets is selected as the reference image dataset. A movement matrix is then calculated from each of the other 3D image datasets in relation to the reference image dataset. What is referred to as a movement matrix (below, also "movement field") is a three-dimensional vector field by means of which voxels or groups thereof in one 3D image dataset are linked to voxels or groups thereof in the other 3D image dataset. The movement matrix therein characterizes a "movement", which is to say a spatial change in mutually corresponding image structures between the first 3D image dataset serving as the starting point and the second 3D image dataset. A correlation method, for example what is termed block matching known per se, or a method based on optical flow, is preferably used for calculating the movement matrix from the two 3D image datasets.

The movement matrix is in the method described in DE 10 2004 048 209 B3 subsequently employed for deforming the preliminary 3D image datasets. In other words, the preliminary 3D image datasets that have been assigned to any heartbeat phases are imaged onto the reference image dataset's situation. With the aid of the movement field, back-calculating is as it were performed from the 3D image dataset so that the situation prevailing during the heartbeat phase for which the reference image dataset was defined will be imaged. The defined preliminary 3D image datasets are then added together and a final 3D image dataset is obtained.

SUMMARY OF THE INVENTION

The object of the present invention is to develop the approaches known from the prior art so as to achieve an as good as possible imaging quality, which is to say good image definition accompanied by as great as possible freedom from noise, and to do so with an as good as possible time resolution.

Said object is achieved by a method having the features according to the claims.

The inventive method thus comprises the steps:

a) Recording a sequence of 2D X-ray images of the heart for each of which the heartbeat phase at the instant of image recording is measured so that each 2D X-ray image thus obtained has been assigned a heartbeat phase, b) dividing the range of possible heartbeat phases into intervals, c) through reconstruction, generating a 3D image dataset for each interval from the 2D X-ray images that have each been assigned to a heartbeat phase from the interval, and assigning each 3D image dataset to a heartbeat phase from the respective interval, d) selecting one of the generated 3D image datasets as a reference image dataset,
e) calculating the movement field of each of the other 3D image datasets relative to the reference image dataset,
f) at least twice performing the following steps:
   f1) Selecting a heartbeat phase,
   f2) selecting at least one 2D X-ray image that has been assigned to the heartbeat phase selected at step f1) or has been assigned to a heartbeat phase situated within an interval around the heartbeat phase selected at step f1) that is shorter than the intervals defined at step b),
   f3) through reconstruction, generating a 3D image dataset from all 2D X-ray images selected at step f2),
   f4) determining the position of the heartbeat phase relative to the heartbeat phases that were assigned at step c) to the 3D image dataset, and, using said determined relative position, determining or calculating an interpolated movement field for the 3D image dataset generated at step f3) relative to the reference image dataset on the basis of the movement fields calculated at step e),
   f5) using the interpolated movement field determined or calculated at step f4) for deforming the 3D image dataset generated at step f3),
g) summating the deformed 3D image datasets each generated during the performance of step f5) in order thereby to obtain the 3D X-ray image dataset requiring to be provided.

The invention centers on no longer employing, as in DE 10 2004 048 209 B3, the selfsame 3D image datasets (therein referred to as preliminary 3D image datasets) for calculating the individual movement fields on the one hand and, on the other, for generating the deformed 3D image datasets. Instead, the invention separates said two aspects. The invention therein utilizes the knowledge that a relatively large volume of data initially has to be available for calculating the movement fields so that the intervals must have been selected relatively coarsely at step b), but that the data ultimately used for the 3D X-ray image dataset requiring to be provided can be selected much more finely or edited more targetedly once the movement fields have been calculated. Step f2) even allows just one 2D X-ray image to be selected from which a 3D image dataset can be generated at step f3) likewise in accordance with filtered back-projection. To make this improvement on the prior art possible, the calculated movement fields are no longer exclusively worked with directly. A respective movement field is instead targetedly calculated for a specific heartbeat phase through interpolation.

If, for example, there is a first movement field for a first heartbeat phase and a second movement field for a second heartbeat phase, and if the movement field is to be calculated for a heartbeat phase situated precisely between said two heartbeat phases, then precisely one mean value of the movement field's vectors can be used. If a vector in the first movement field points from a first voxel to a second voxel and if the second voxel in the second movement field has not been assigned a vector (a zero vector), then the vector will in the interpolated movement field point from the first voxel to a voxel situated precisely between the first voxel and second voxel. The 3D image datasets that have been generated from one or at most just a few X-ray images can through interpolating of the movement fields be deformed much more precisely at step f5). Structures of the heart will consequently be imaged more accurately in the summated 3D X-ray image dataset. The inventive method is further characterized in that the 3D X-ray image dataset provided has a particularly large signal-to-noise ratio.

Although a linear interpolation is preferably used, an interpolation using what are termed cubic splines is also possible.

It may occasionally happen that a heartbeat phase is selected that has been assigned a 3D image dataset at step c) so that a movement field from step e) will already exist precisely for said heartbeat phase. The interpolation may in that eventuality possibly include taking over precisely the unchanged movement field. A heartbeat phase that was not assigned a 3D image dataset at step c) is, of course, preferably selected at step f1) during at least one pass of the sequence of steps f).

The heartbeat phases are preferably traversed as systematically as possible so that the X-ray images that have been recorded are used as fully as possible. Thus the range of possible heartbeat phases can in the sequence of steps f) be divided into a number of intervals that is greater than the number of intervals from step b), with steps f1) to f5) then being performed for each interval thus obtained. One heartbeat phase is during each traversal selected at step f1) from one of said intervals, and specifically each time from another of said intervals. The selected heartbeat phase is preferably a mid heartbeat phase in the respective interval.

The invention can particularly advantageously utilize the method that was explained in the introduction and in the case of which further traversals after one traversal are triggered based on the heartbeat phase (see also the aforementioned article by G. Lauritsch et al.). In other words, the sequence of 2D X-ray images is recorded with the aid of an X-ray C-arm that repeatedly traverses a predetermined number of fixed angular positions within a specific time, with the further traversals after the first traversal each being triggered as a function of the heartbeat phase in such a way that, with a specific interval of heartbeat phases being specified, at least one X-ray image that has been assigned a heartbeat phase from said interval will be recorded at each angular position. The assigning of X-ray images to heartbeat phases will be optimized thereby, as a result of which the quality of the resulting 3D X-ray image dataset will be especially high, with regard especially also to time resolution.

As already mentioned above, the fact that the X-ray C-arm executes N traversals means that the predetermined interval occupies precisely one N-th part of the entire range of heartbeat phases.

In the method described hitherto, the 3D image datasets from step f3) are each deformed at step f5) such as to be imaged onto the reference image dataset in relation to which the movement fields have been defined. If it is desired not to be constrained by that single characterization of the reference image dataset, it is also possible to select any target heartbeat phase that is different from that assigned to the reference image dataset. With the aid of the movement fields determined at step e), which only need to be reversed in their vector direction, it will be then be possible, proceeding from the 3D X-ray image dataset obtained at step g), to calculate a 3D X-ray image dataset that is assigned precisely to the target heartbeat phase, once again through interpolation, this time of the reversed movement fields.

The target heartbeat phase can be any heartbeat phase. It will then be possible to show the heart's motion in any heartbeat phases.

The target heartbeat phase can also be a heartbeat phase that has been assigned to a 2D image or a 3D image dataset other than the images or image datasets employed in the method described hitherto. The other 2D image or 3D image dataset does not have to consist of X-ray images, its rather being the case that, for example, nuclear magnetic resonance images can also be used. Once the 3D X-ray image dataset from step g) has been deformed, the same can then be registered with the 2D image (3D-2D registering) or with the 3D image dataset (3D-3D registering). Two different types of image data are, as is known, imaged positionally and dimensionally correctly one upon the other during registering. That is done working with image recognition, with highlighted structures in the images each being recognized and an imaging rule determined for transposing from one dataset to the other. Registering methods of such type can be used to practical advantage for the further use of different datasets jointly, for example when imaging structures from different datasets are to be shown superimposed.

The movement fields do not necessarily have to await calculation at sub-step f4) but can also be made available ahead of the sequence of steps f). That will be of practical advantage especially when a large number of heartbeat phases are encompassed within the scope of the sequence of steps f), for example when all (or at least most) X-ray images are used. A 4D dataset of movement fields can then through interpolation be calculated ahead of the sequence of steps f) as a function of the heartbeat phase from the movement fields determined at step e), and at sub-step f4) only the respectively interpolated movement field will then have to be determined from said 4D dataset so that said field can be used at step f5).

Advance provisioning of the 4D dataset of movement fields has the advantage of allowing the movement fields to be edited in advance. For example they can undergo smoothing through the application of filters known per se. Artifacts will be suppressed thereby.

BRIEF DESCRIPTION OF THE DRAWINGS

A preferred embodiment of the invention is described below with reference to the drawing.

DETAILED DESCRIPTION OF THE INVENTION

Figure 1:
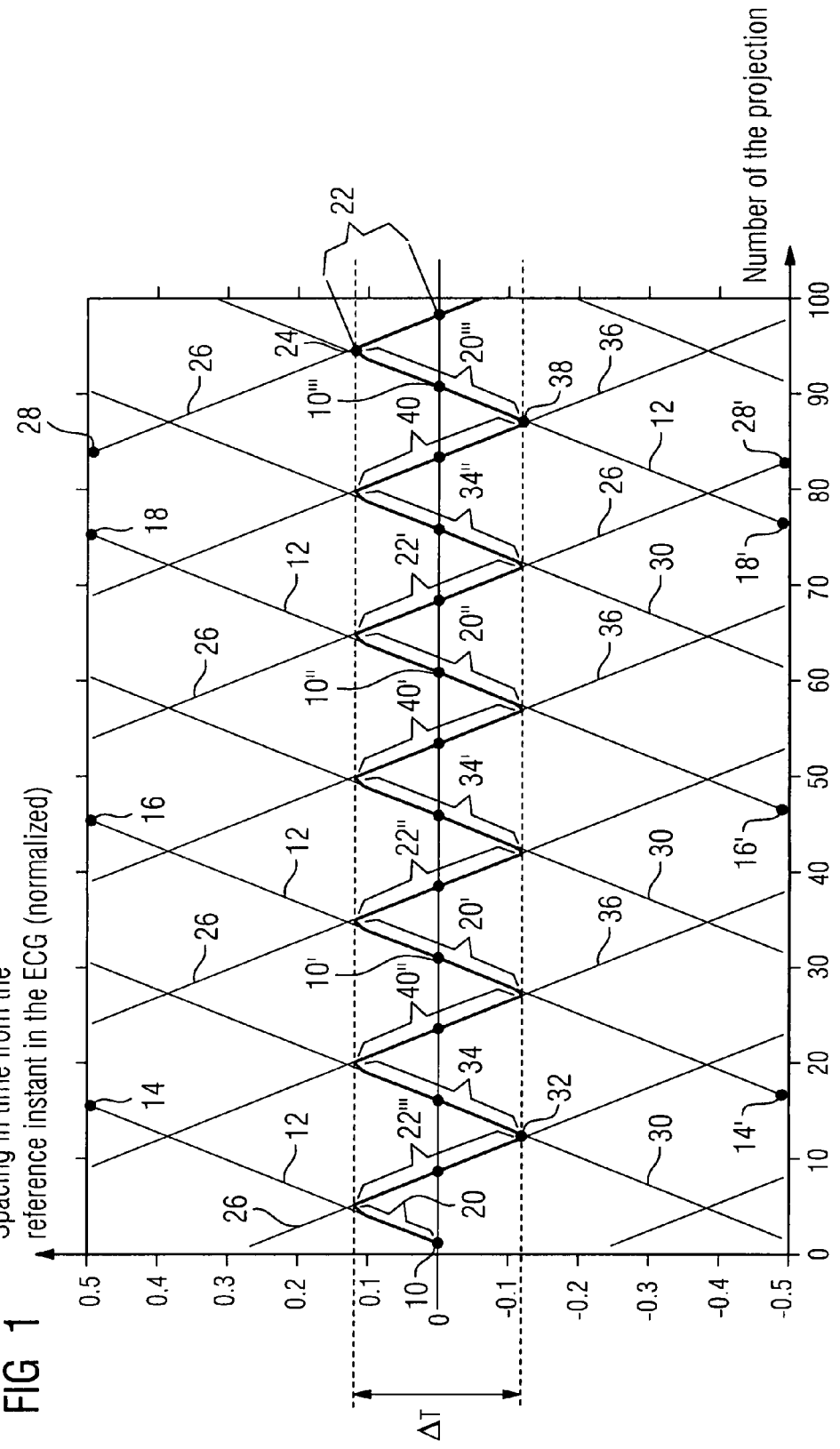
FIG. 1 shows an idealized representation of the heartbeat phases as a function of the projection angle of an X-ray C-arm used for recording 2D X-ray images, FIG. 2 serves to elucidate a limited version of the inventive method with the aid of the representation shown in FIG. 1, and FIG. 3 serves to elucidate an expanded version of the inventive method with the aid of the representation shown in FIG. 1.

Assume that a patient is located in a manner known per se in a C-arm X-ray system. Attached at opposite points to the X-ray C-arm are an X-ray source and an X-ray detector. The X-ray C-arm can be moved to well-defined angular positions. An image from a specific angular position is referred to as a "projection". The projections are in FIG. 1 counted successively along the x-axis. An electrocardiogram is taken of the patient. The regular heartbeat results, as is known, in regular structures in the electrocardiogram. A reference structure can be determined within each period and a cardiac phase determined in relation to said reference structure. The cardiac phase is the spacing in time from the respective reference instant which the reference structure has. Said spacing is in FIG. 1 plotted on the y-axis. The spacing in time between two such reference instants has here been normalized at "1". If the spacing in time is in each case measured relative to the closest reference instant, the result will be a measuring range of −0.5 to +0.5, as shown in FIG. 1.

Assume that a traversal of the X-ray C-arm is now started precisely at the reference instant. A first X-ray image 10 will in that way be obtained which in FIG. 1 has the coordinates: Projection 1, spacing in time 0. If the X-ray C-arm is moved evenly, the result will be a linear relationship in accordance with the straight lines 12. In keeping with the change in the reference instant, there will be a jump from +0.5 to −0.5 between the points 14 and 14', then between the points 16 and 16', and later between the points 18 and 18'. The curve in between remains in each case straight, see the reference numeral 12. Assume now that with the aid of the X-ray images the heart's behavior is to be observed in a specific heartbeat phase corresponding precisely to the reference instant. Precisely for that phase, apart from the image 10 there are also the images whose coordinates are referenced 10', 10'', 10'''. Four images are a modest yield in view of the 100 projections recorded. So what will then be done is to select an interval ΔT around the reference instant at which it is assumed that the X-ray images will show structures not deviating too much from those desired. It will thus be possible to use the, in each case, sections 20, 20', 20'', 20''' of the straight line 12 that are situated precisely within the interval ΔT. That is in itself an advance compared with selecting the individual X-ray images having the coordinates 10, 10', 10'', 10'''. It is, though, desirable also to close the gaps between the sections 20, 20', 20'', 20'''. That is enabled by four different traversals: Proceeding from the final position at the projection 100, a traversal of the X-ray C-arm in the opposite direction is first started. That is then triggered precisely such that a section 22 of the straight line will end at the same point 24 as the section 20'''. To make said triggering possible, it is necessary only for the apparatus recording the electrocardiogram to be coupled to the X-ray C-arm control system. The section 22 resumes beyond the point 24 in a straight lines 26. There is a jump between the points 28 and 28', then the straight line 26 resumes again and once more traverses the interval ΔT with a section 22'. The straight line 26 then in its further course also traverses the interval ΔT with a section 22'' and 22'''. There are now X-ray images having an associated heartbeat phase within the interval ΔT for half the projections (angular positions). Two further traversals are performed that are likewise triggered using the heartbeat. In the same way that section 22 ended precisely at the point 24, it is now provided for the X-ray C-arm to be moved in such a way that a straight line 30 will precisely traverse the point 32 so that a section 34 will be joined to the section 22'''. If the X-ray C-arm is moved back, a triggering will then likewise take place: A straight line 36 will be traversed in such a way that it will be joined precisely at the point 38 to the section 22''' and a section 40 will close precisely the gap. The same applies to the sections 40' and 40'', each of which the straight line 36 will traverse when passing through the interval ΔT. The sequence of sections 20, 22''', 34, 40''', 20' etc. drawn with heavier lining will thus be obtained after four complete traversals of the X-ray C-arm (straight lines 12, 26, 30, and 36). It is made clear that precisely each projection, which is to say each angular position, was traversed once for heartbeat phases within the interval ΔT. There having been a total of four traversals of the X-ray C-arm, the interval ΔT will also extend precisely across a fourth of the total range, namely from −0.125 to +0.125. Precisely four such intervals can incidentally be defined in which a zigzag sequence of similar kind can be drawn, namely from +0.125 to +0.375, from −0.375 to −0.125, and also from +0.375 via 0.5/−0.5 to −0.375.

For each of said intervals there will thus be one X-ray image in each case for each angular position. Said intervals can hence in a preferable manner serve for generating 3D reconstructions of the 2D X-ray images (of the projections, therefore). Each individual 2D X-ray image therein undergoes a filtered back-projection process, and the filtered back-projections generated thereby are added together for each interval. Four 3D image datasets will then be obtained, one for each interval. Said four 3D image datasets can each be assigned to a heartbeat phase. A mid cardiac phase is preferably assigned, thus in the case of the interval shown in FIG. 1 the heartbeat phase 0. In the case of the other, aforementioned intervals the mid heartbeat phases are +0.25, +0.5=−0.5, and −0.25. An attempt is then made to find an imaging rule for the four 3D image datasets relative to each other for ensuing applications of X-ray images to heartbeat phases beyond the interval shown in FIG. 1. Assume that the image dataset for the interval ΔT shown in FIG. 1 around the heartbeat phase 0 is selected as the reference image dataset. An imaging rule of said type can be determined using correlation methods, for example elastic registering. What is obtained as a dataset is what is termed a movement field for each of the 3D image datasets for those of the heartbeat-phase intervals not shown in FIG. 1. A movement field having the entries 0 can pro forma be defined for the heartbeat phase 0.

Figure 2:
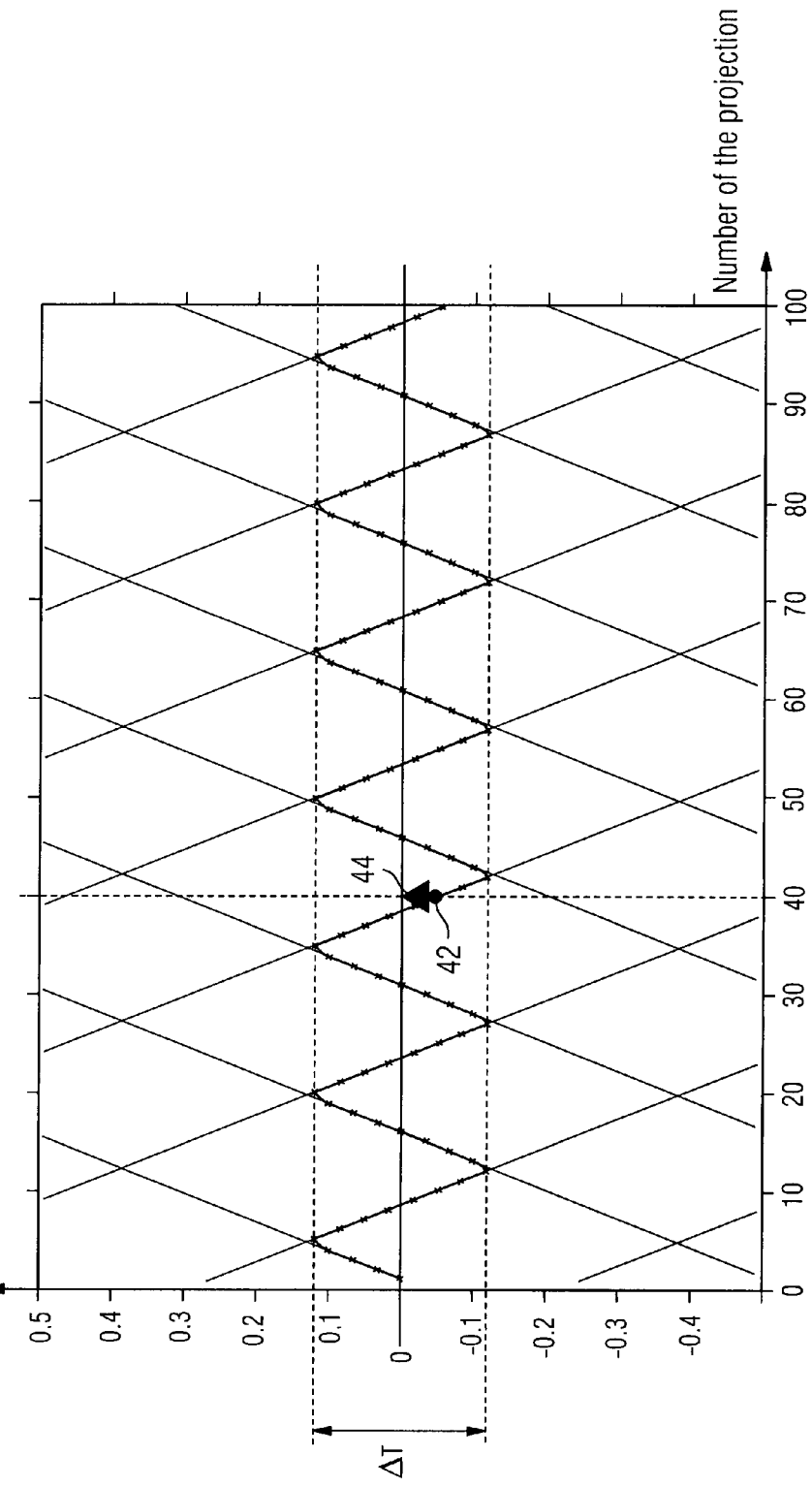

Said movement fields can then be used as follows: FIG. 2 again shows the chart illustrated in FIG. 1, with the curve highlighted in FIG. 1 with heavy lining this time being shown discretized: Individual crosses correspond to individual X-ray images. The individual X-ray images for which a cross is shown in FIG. 2, meaning which have been assigned a heartbeat phase within the interval ΔT around the heartbeat phase 0, are all to be used. Whereas it was above described that all X-ray images assigned a heartbeat phase from an interval were used for the respective reconstruction of a 3D image dataset, a refinement is now to take place to the effect that a distinction will be made between different heartbeat phases within the interval ΔT. Assume that one X-ray image is taken out that is identified by the point referenced 42 in FIG. 2. The X-ray image identified by 42 has been assigned a heartbeat phase different from 0. If it is wished to obtain a 3D image dataset assigned precisely to the heartbeat phase 0, then it will be advantageous for matching to take place. To that end, the X-ray image first undergoes a filtered back-projection process so that a 3D image dataset will be obtained. Said 3D image dataset is then deformed, with calculating being performed through deforming from the negative heartbeat phase belonging to the X-ray image 42 toward the heartbeat phase 0 (meaning that a back-calculation or, in the present case rather an advance calculation, will be performed). That is illustrated by the arrow referenced 44 in FIG. 2. What is termed deforming of the 3D image dataset uses the movement fields that have been calculated in accordance with the above description. The heartbeat phase belonging to the X-ray image 42 is in the present case situated between the heartbeat phase 0 and the heartbeat phase −0.25. The movement fields for the intervals centered around the heartbeat phase 0 or, as the case may be, the heartbeat phase −0.25 can then be used. Since the heartbeat phase belonging to the X-ray image 42 is closer to the heartbeat phase 0, the movement field belonging to the heartbeat phase 0 (and hence having the entries 0, of course) will be weighted more heavily than the movement field belonging to the interval centered around the heartbeat phase −0.25. Said weighting can be taken into account using a simple interpolation method. What is interpolated are the vector entries of the movement field across the spacing in time relative to the reference instant in the ECG.

Thus whereas the X-ray images were previously copied while the 3D image datasets were being determined and all X-ray images in the group were treated equally, the X-ray images are now treated individually so that the heartbeat phase can be included precisely during deforming.

The X-ray images identified by crosses in FIG. 2 are in a first method used exclusively. A deformed 3D back-projection is obtained using each X-ray image, and the deformed 3D back-projections can be added together so that a 3D image dataset is once again obtained. The 3D image dataset is characterized in that precisely one X-ray image has been used at each angular position.

The image quality, in particular the definition in the 3D X-ray image dataset thus obtained, is particularly good.

For progressing the embodiment explained with the aid of FIG. 2, all recorded X-ray images can be used. That is explained with the aid of FIG. 3. That again shows the content of FIG. 1, but with all recorded X-ray images being identified by a cross.

Again to be generated is a 3D image dataset reproducing the situation at a heartbeat phase 0. By means of filtered back-projection a 3D image dataset is again obtained from projections, meaning from 2D X-ray images, that undergoes a deformation step in order thereby to achieve imaging onto the heartbeat phase 0. Use is therein again made of the movement fields, with an interpolation as a rule being employed. In contrast to the embodiment discussed with the aid of FIG. 2, the X-ray images whose assigned heartbeat phase is situated within the interval ΔT are now no longer used exclusively. Rather it is the case that four X-ray images identified by the points 46, 48, 50, and 52 are used at a predetermined angular position. The arrows 54 and 56 indicate that said X-ray images will when filtered back-projection has been performed be imaged onto the heartbeat phase 0. In contrast to the embodiment discussed with the aid of FIG. 2, four times as many X-ray images are therefore used. The signal-to-noise ratio will be further increased thereby. If all X-ray images at all angular positions are used, it will mean that no X-ray image will remain unused. The method will thereby be rendered extremely efficient.

The movement fields can incidentally be further utilized: If a 3D X-ray image dataset is required for a heartbeat phase different from 0, then a movement field can be interpolated precisely for said heartbeat phase based on the four movement fields precisely for the required heartbeat phase. The 3D X-ray image dataset based on all X-ray images can then be transformed with the aid of said movement field, which is to say can once again be deformed. With the aid of the movement fields it is thus possible to calculate the 3D image dataset for any heartbeat phases so that a four-dimensional dataset (3D image dataset having the heartbeat phase as the fourth dimension) can be obtained.

With the inventive method, the image quality is significantly enhanced compared with the methods according to the prior art. The overall effort required can consequently also be reduced where applicable: It is possible thanks to the computational measure applied within the scope of the present invention to with four X-ray C-arm traversals obtain an image quality which in the prior art will perhaps have been achieved only after eight or twelve X-ray C-arm traversals. Structures can in part be resolved which in the prior art have not been resolvable at all.

The invention claimed is:

1. A method for generating a 3D X-ray image dataset of a heart of a patient, comprising:
   recording a sequence of 2D X-ray images of the heart with heartbeat phases at image recording instants being measured and assigned to the images;
   dividing a range of the heartbeat phases into a plurality of intervals;

generating a plurality of 3D image datasets, each 3D image dataset being generated from the 2D X-ray images assigned to a heartbeat phrase from a respective interval;

assigning each 3D image dataset to the heartbeat phase from the respective interval;

choosing one of the 3D image datasets as a reference image dataset;

calculating movement fields of remaining 3D image datasets relative to the reference image dataset;

selecting a heartbeat phase from the heartbeat phases;

picking a 2D X-ray image assigned to the selected heartbeat phase;

generating a second 3D image dataset from the picked 2D X-ray image;

determining a position of the selected heartbeat phase relative to the heartbeat phases;

calculating an interpolated movement field for the second 3D image dataset relative to the reference image dataset based on the movement fields and the position; and deforming the second 3D image dataset using the interpolated movement field to generate the 3D X-ray image dataset.

2. The method as claimed in claim 1, wherein a further heartbeat phase is selected and a third 3D image dataset is deformed for the further selected heartbeat phase, and wherein the 3D X-ray image dataset is generated by summing the deformed second and the deformed third image dataset.

3. The method as claimed in claim 2, wherein at least one of the heartbeat phase and the further heartbeat phase is not assigned to one of the 3D image datasets.

4. The method as claimed in claim 1, wherein the range of the heartbeat phases is divided into a further plurality of intervals that is narrower than the intervals for selecting the heartbeat phase.

5. The method as claimed in claim 1, wherein the sequence of 2D X-ray images is recorded by an X-ray C-arm that repeatedly traverses a predetermined number of fixed angular positions within a specific time, wherein the traversal is triggered as a function of the heartbeat phases so that in a specific interval at least one 2D X-ray image assigned to the heartbeat phase from the specific interval will be recorded at each angular position.

6. The method as claimed in claim 5, wherein the range of heartbeat phases is divided into the intervals of the predetermined number of fixed angular positions.

7. The method as claimed in claim 1, wherein a target heartbeat phase is selected that is different from a heartbeat phase assigned to the reference image dataset, wherein the movement fields are reversed, and wherein the interpolated movement field is calculated for the target heartbeat phase based on the reversed movement fields for the deforming.

8. The method as claimed in claim 7, wherein the target heartbeat phase is selected from any of the heartbeat phases.

9. The method as claimed in claim 7, wherein the target heartbeat phase is a heartbeat phase assigned to a further 2D image or a further 3D image dataset other than the recorded 2D X-ray images, or the 3D image datasets or the second 3D image dataset, and wherein the deformed 3D X-ray image dataset is registered with the further 2D image or the further 3D image dataset.

10. The method as claimed in claim 1, wherein the movement fields are interpolated to calculate a 4D movement field before selecting the heartbeat phase.

11. The method as claimed in claim 1, wherein the 4D movement field is smoothed through a filter application before selecting the heartbeat phase.

12. The method as claimed in claim 1, wherein the 2D X-ray image is picked from images assigned to a heartbeat phase from an interval that is closer to an interval from the selected heartbeat phase than the other intervals to the interval from the selected heartbeat phase.

13. An X-ray device for generating a 3D X-ray image dataset of a heart of a patient, comprising:

an X-ray source that emits X-rays to the patient;

an X-ray detector that records a sequence of 2D X-ray images of the heart with heartbeat phases at image recording instants being measured and assigned to the images; and a computing device that:

divides a range of the heartbeat phases into a plurality of intervals, generates a plurality of 3D image datasets, each 3D image dataset being generated from the 2D X-ray images assigned to a heartbeat phrase from a respective interval, assigns each 3D image dataset to the heartbeat phase from the respective interval, chooses one of the 3D image datasets as a reference image dataset, calculates movement fields of remaining 3D image datasets relative to the reference image dataset, selects a heartbeat phase from the heartbeat phases, picks a 2D X-ray image assigned to the selected heartbeat phase, generates a second 3D image dataset from the picked 2D X-ray image, determines a position of the selected heartbeat phase relative to the heartbeat phases, calculates an interpolated movement field for the second 3D image dataset relative to the reference image dataset based on the movement fields and the position, and deforms the second 3D image dataset using the interpolated movement field to generate the 3D X-ray image dataset.

14. The X-ray device as claimed in claim 13, wherein a further heartbeat phase is selected and a third 3D image dataset is deformed for the further selected heartbeat phase, and wherein the 3D X-ray image dataset is generated by summing the deformed second and the deformed third image dataset.

* * * * *